United States Patent
Zhe et al.

(10) Patent No.: US 9,797,851 B2
(45) Date of Patent: Oct. 24, 2017

(54) INTEGRATED ULTRASONIC-INDUCTIVE PULSE SENSOR FOR WEAR DEBRIS DETECTION

(71) Applicants: Jiang Zhe, Copley, OH (US); Li Du, Akron, OH (US)

(72) Inventors: Jiang Zhe, Copley, OH (US); Li Du, Akron, OH (US)

(73) Assignee: The University of Akron, Akron, OH (US)

( * ) Notice: Subject to any disclaimer, the term of this patent is extended or adjusted under 35 U.S.C. 154(b) by 653 days.

(21) Appl. No.: 14/092,436

(22) Filed: Nov. 27, 2013

(65) Prior Publication Data

US 2014/0144216 A1    May 29, 2014

Related U.S. Application Data

(60) Provisional application No. 61/730,225, filed on Nov. 27, 2012.

(51) Int. Cl.
  *G01N 27/02*    (2006.01)
  *G01N 29/024*   (2006.01)
  *G01N 29/22*    (2006.01)
  *G01N 33/28*    (2006.01)

(52) U.S. Cl.
  CPC ......... *G01N 27/023* (2013.01); *G01N 29/024* (2013.01); *G01N 29/222* (2013.01); *G01N 33/2888* (2013.01); *G01N 2291/02416* (2013.01)

(58) Field of Classification Search
  CPC .... G01N 27/023; G01N 29/02; G01N 29/024; G01N 29/221; G01N 29/222; G01N 2291/02416; G01N 33/2888

USPC .... 73/61.71, 597, 598, 627, 628, 629, 570.5
See application file for complete search history.

(56) References Cited

U.S. PATENT DOCUMENTS

| | | | | |
|---|---|---|---|---|
| 4,509,360 A * | 4/1985 | Erwin | .................. | G01N 29/032 73/599 |
| 5,723,773 A * | 3/1998 | Bryan | .................. | G01N 29/032 310/323.18 |
| 6,216,538 B1 * | 4/2001 | Yasuda | ................ | B01D 21/283 210/748.05 |
| 6,786,096 B2 * | 9/2004 | Bond | ..................... | G01N 21/59 73/598 |

(Continued)

*Primary Examiner* — Daniel S Larkin
(74) *Attorney, Agent, or Firm* — Renner Kenner Greive Bobak Taylor & Weber

(57) ABSTRACT

An apparatus for detecting wear particles in a fluid includes an inlet channel and an outlet channel. An ultrasonic transducer creating an acoustic wave that defines an acoustic focal zone is located between the inlet and outlet channels. A flow path located between the inlet and outlet channel is shaped to restrict the flow of the fluid to be within the acoustic focal zone. An inductive pulse sensor includes a plurality of flow channels receiving the fluid and a plurality of planar coils wound around the flow channels. The inductive pulse sensor includes a detection system for the detection of wear particles passing through the flow channels based on a change in an electrical property of the planar coils. A single combined excitation signal is sent to all the planar coils at once and the detection system measures one single output measurement for the plurality of flow channels.

15 Claims, 6 Drawing Sheets

(56) References Cited

U.S. PATENT DOCUMENTS

| | | | |
|---|---|---|---|
| 7,340,957 B2* | 3/2008 | Kaduchak | G01N 15/1459 |
| | | | 73/570.5 |
| 2004/0069065 A1* | 4/2004 | Tallon | G01H 5/00 |
| | | | 73/597 |
| 2008/0028838 A1* | 2/2008 | Andersen | G01N 29/046 |
| | | | 73/61.73 |
| 2010/0109686 A1* | 5/2010 | Zhe | G01M 13/02 |
| | | | 324/698 |

* cited by examiner

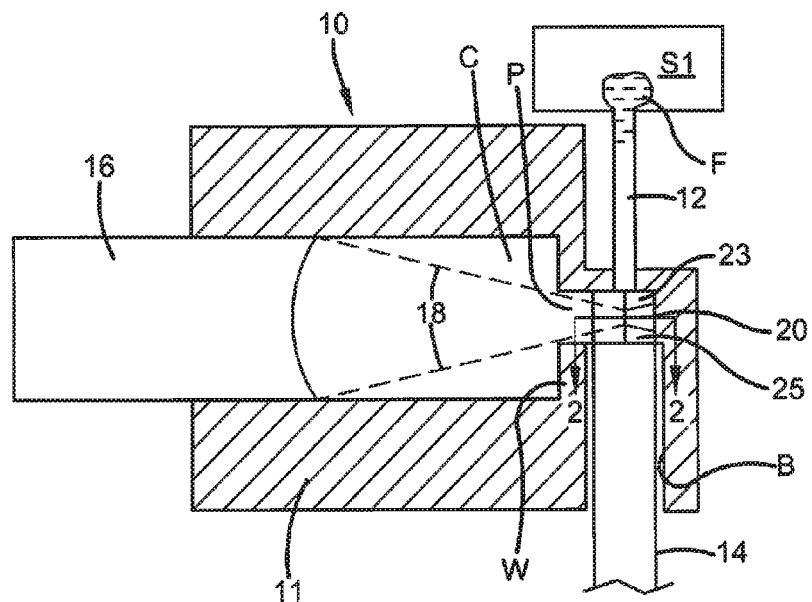
FIG. 1
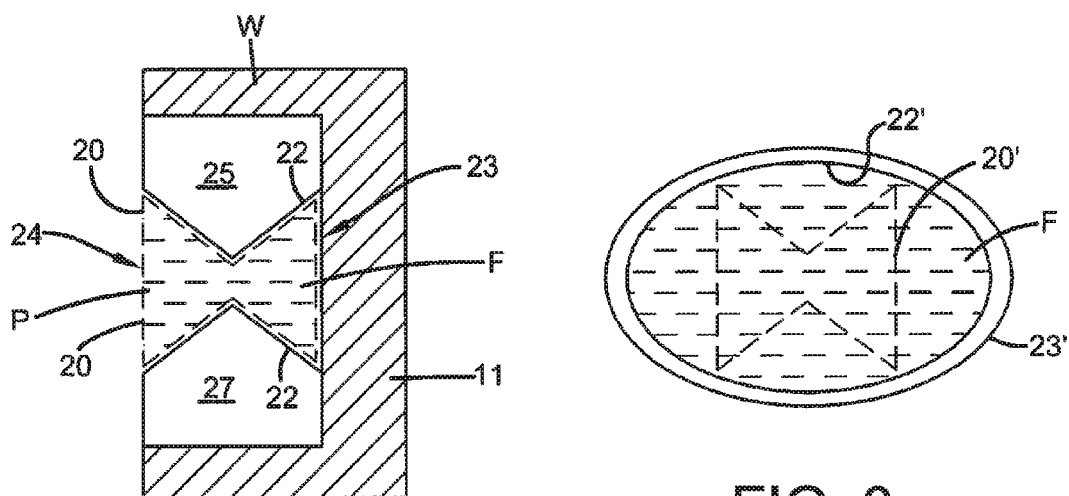
FIG. 2
FIG. 3
PRIOR ART

INTEGRATED ULTRASONIC-INDUCTIVE PULSE SENSOR FOR WEAR DEBRIS DETECTION

CROSS-REFERENCE TO RELATED APPLICATIONS

This application claims the benefit of U.S. provisional patent application Ser. No. 61/730,225 entitled "An Integrated Ultrasonic-Inductive Pulse Sensor for Wear Debris Detection," filed Nov. 27, 2012, and incorporated by reference in its entirety.

FIELD OF THE INVENTION

The present invention generally relates to an apparatus and a method for detection of wear particles in a lubricant. Some embodiments relate to an apparatus employing an ultrasonic transducer to detect wear particles in a fluid forced to flow through a focal zone of the ultrasonic wave generated by the transducer. Other embodiments relate to an apparatus employing an inductive pulse sensor multiplexed and multichannel detection. More particularly, the present invention relates to an apparatus and method of detecting wear particles in a lubricant which uses both an ultrasonic detection means which employs a multiplexed and multichannel detection means, and an inductive pulse detection means.

BACKGROUND OF THE INVENTION

Machine parts, such as aircraft engines and gear boxes in which components move relative to each other, are often lubricated with a lubricant oil to reduce wear. Over time, small wear particles break off from machine components and build up in the oil. These wear particles generally begin with sizes in the range of 1-10 microns, but, when abnormal wear begins, larger particles, in the range of 10 to 50 microns are generated. The particle population and size of the particles tends to increase over time until eventually, a machine failure can result.

To monitor the change in lubricant wear particles, samples of the oil may be withdrawn from the machine at scheduled times and sent to a laboratory for analysis. A variety of off-line methods exist for measuring properties of lubricating fluids. For example, the suspended particles may be separated from the oil sample (e.g., by using a rotary particle depositor) and then quantified. Another method involves placing the oil sample in a container and creating a magnetic flux field using a sensing electromagnetic coil. The distortion of the flux field caused by the particle burden is then noted as a numerical Particle Quantifying (PQ) value (see U.S. Pat. No. 5,404,100). However, each of these methods takes time to generate wear information. As a result, critical failures of machines may occur even when samples are sent regularly for testing.

There are currently known apparatuses and methods of detecting lubricating oil debris, both ferrous and non-ferrous. The apparatus and method taught in U.S. Pat. No. 8,522,604 uses a single microchannel and an inductive pulse sensor to detect and count all metallic debris based on the inductive Coulter counting principle. However, this apparatus and method of detecting debris has two faults—it cannot detect non-metallic debris and it lacks the ability to incorporate multiple channels for higher throughput of data collection. Wear particle detection apparatus would benefit from the ability to detect non-metallic debris because many modern machine parts have components that are made of a non-metallic material such as plastic. In this context, the art would also benefit from being able to discern between metallic and non-metallic wear particles. The art would also benefit from the ability to use a multiplexed and multichannel inductive sensor because this will allow for a higher throughput of micro scale debris particles. Therefore, there remains a need for an apparatus and method which permits in-situ testing of lubricants that can detect both metallic and non-metallic debris and which has the ability to incorporate a multiplexed and multichannel inductive sensor which will use only one set of detection electronics.

SUMMARY OF THE INVENTION

A first embodiment of this invention provides an apparatus for the detection of wear particles in a fluid comprising of: an inlet channel receiving a fluid having wear particles therein; an outlet channel, wherein said fluid flows from said inlet channel to said outlet channel; an ultrasonic transducer creating an acoustic wave that defines an acoustic focal zone between said inlet channel and said outlet channel; and a flow path between said inlet channel and said outlet channel wherein said flow path is shaped to restrict the flow of said fluid to be wholly within said acoustic focal zone of said ultrasonic transducer.

A second embodiment of this invention provides an apparatus as in the first embodiment, further comprising an inductive pulse sensor comprising a planar coil wound around the inlet channel and a detection system for detecting wear particles passing through the inlet channel based on a change in an electrical property of said planer coil as a wear particle passes said planar coil.

A third embodiment of this invention provides an apparatus as in any either the first or second embodiment further comprising an inductive pulse sensor comprising a planar coil wound around the outlet channel and a detection system for detecting wear particles passing through the inlet channel based on a change in an electrical property of said planer coil as a wear particle passes said planar coil.

A fourth embodiment of this invention provides an apparatus as in the first through third embodiments wherein said ultrasonic transducer is a point focused ultrasonic transducer.

A fifth embodiment of this invention provides an apparatus as in the first through fourth embodiments wherein said ultrasonic transducer is a line focused ultrasonic transducer.

A sixth embodiment of this invention provides an apparatus as in the first through fifth embodiments wherein said ultrasonic transducer is a point focused ultrasonic transducer; wherein said acoustic focal zone is in the shape of an hourglass; and wherein said flow path is in the shape of an hourglass.

A seventh embodiment of this invention provides an apparatus for the detection of wear particles in a fluid comprising of: an inductive pulse sensor comprising of: a plurality of flow channels receiving a fluid having wear particles therein; a plurality of planar coils wound around said plurality of flow channels and wherein said plurality of planar coils are in series with one another; an outlet channel, wherein said fluid flows from said plurality of flow channels to said outlet channel; and a detection system for the detection of wear particles passing through said plurality of flow channels based on a change in an electrical property of said planar coils as a wear particle(s) passes said planar coils and wherein a single combined excitation signal is sent to all of said planar coils at once and said detection system measures one single output measurement for said plurality of flow channels.

A eighth embodiment of this invention provides an apparatus for the detection of wear particles in a fluid comprising of: an inlet channel receiving a fluid having wear particles therein; an outlet channel, wherein said fluid flows from said inlet channel to said outlet channel; an ultrasonic transducer creating an acoustic wave that defines an acoustic focal zone between said inlet channel and said outlet channel; a flow path between said inlet channel and said outlet channel wherein said flow path is shaped to restrict the flow of said fluid to be wholly within said acoustic focal zone of said ultrasonic transducer; and e. an inductive pulse sensor comprising of: a plurality of flow channels receiving the fluid having wear particles therein; a plurality of planar coils wound around said plurality of flow channels and wherein said plurality of planar coils are in series with one another; and iii. a detection system for the detection of wear particles passing through said plurality of flow channels based on a change in an electrical property of said planar coils as a wear particle(s) passes said planar coils and wherein a single combined excitation signal is sent to all of said planar coils at once and said detection system measures one single output measurement for said plurality of flow channels.

A ninth embodiment of this invention provides an apparatus as in the eighth embodiment wherein said inductive pulse sensor is located upstream of said ultrasonic transducer.

A tenth embodiment of this invention provides an apparatus as in either the eighth or ninth embodiments wherein said inductive pulse sensor is located downstream of said ultrasonic transducer.

An eleventh embodiment of this invention provides an apparatus as in the eighth through tenth embodiments wherein said ultrasonic transducer is a point focused ultrasonic transducer.

A twelfth embodiment of this invention provides an apparatus as in the eighth through eleventh embodiments wherein said ultrasonic transducer is a line focused ultrasonic transducer.

A thirteenth embodiment of this invention provides an apparatus as in the eighth through twelfth embodiments wherein said ultrasonic transducer is a point focused ultrasonic transducer; wherein said acoustic focal zone is in the shape of an hourglass; and wherein said flow path is in the shape of an hourglass

BRIEF DESCRIPTION OF THE DRAWINGS

FIG. 1 is a general schematic view of an apparatus in accordance with a first embodiment of this invention, the apparatus employing an ultrasonic transducer for the detection of wear particles in a fluid;

FIG. 2 is a cross section taken along the line 2-2 in FIG. 1 and showing the flow path shaped commensurate with the focal zone of an ultrasonic transducer;

FIG. 3 is a cross section similar to that of FIG. 2 but showing a prior art flow path that is not commensurate in shape with an ultrasonic transducer focal zone;

DETAILED DESCRIPTION OF ILLUSTRATIVE EMBODIMENTS

Figure 4:
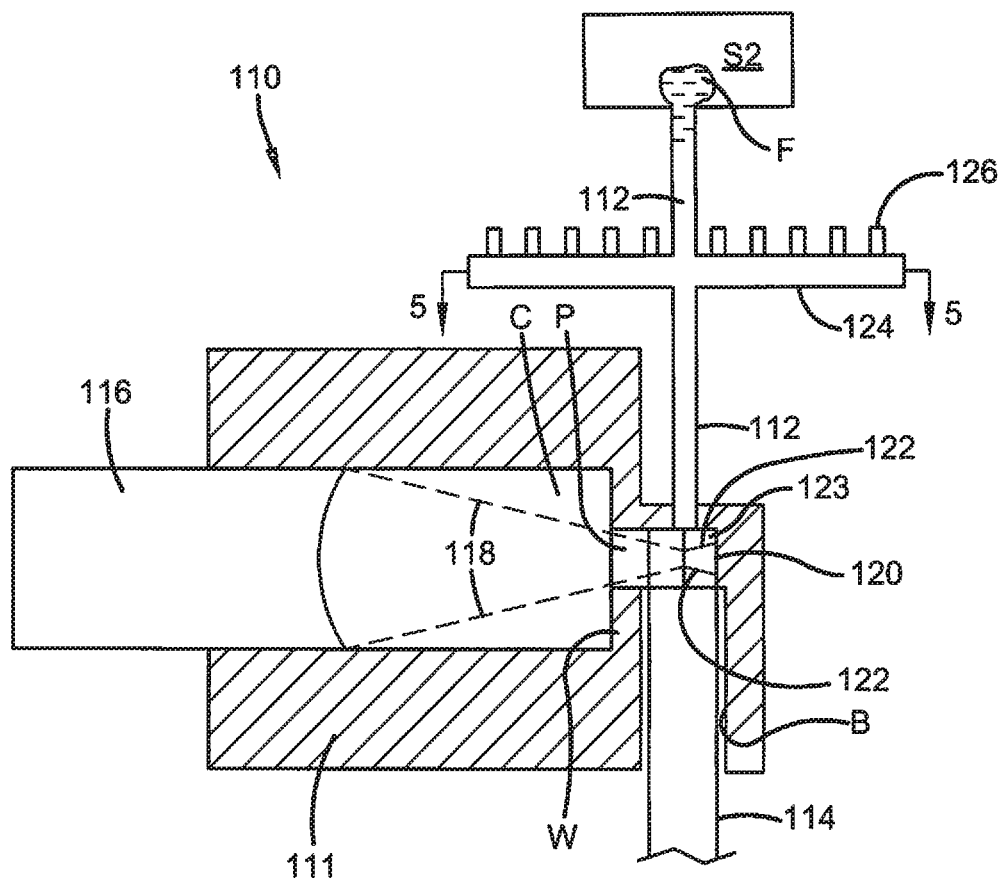
FIG. 4 is a general schematic view of an apparatus in accordance with a second embodiment of this invention, the apparatus employing an ultrasonic transducer for the detection of wear particles in a fluid and employing an inductive pulse sensor upstream of the ultrasonic transducer.

With reference to FIGS. 1 and 2, a first embodiment of this invention provides an apparatus 10 for the detection of wear particles in a fluid. The apparatus 10 includes a housing 11 having a through bore B that receives an inlet channel 12 and an outlet channel 14 with a flow path 22 defined by a flow path structure 23 between the inlet channel 12 and outlet channel 14. Fluid F having wear particles therein is fed into the inlet channel 12 from a source S1 and flows from the inlet channel 12 to the outlet channel 14 through the flow path 22. The housing 11 further includes a transducer chamber C that receives an ultrasonic transducer 16. The transducer chamber C communicates with the through bore B through a wave passage P in a wall W between the through bore B and the transducer chamber C. The ultrasonic transducer 16 creates an acoustic wave 18 that defines an acoustic focal zone 20 at the flow path 22. The flow path 22 is shaped to restrict the flow of the fluid F to be wholly within the acoustic focal zone 20 of the ultrasonic transducer 16. This is the defining characteristic of the flow path 22, and it can be defined by any appropriate flow path structure 23 that confines the flow of fluid F to be wholly within the acoustic focal zone 20. The flow path structure 23 may be a pipe or conduit and can even be an integral part of the inlet channel 12 and outlet channel 14. To facilitate assembly of an apparatus 10, the flow path structure 23 may be defined by separate block structures 25, 27 that together form an appropriately shaped flow path 22, as shown in FIG. 2. The flow path structure 23 has an opening 24 to allow for the unimpeded entrance of the acoustic waves 18 forming the acoustic focal zone 20 at the flow path 22. Different sets of blocks could be employed for providing different flow paths 22 appropriate for a particular amplitude or type of ultrasonic wave 18 and its concomitant focal zone 20.

Fluid F fills the transducer chamber C, inlet channel 12, flow path structure 23 and outlet channel 14, and, with the chamber C filled with fluid F, the fluid F in the transducer chamber C serves as a static barrier to urge the flow of fluid F directly from the inlet channel 12 to the outlet channel 14 through the flow path 22, without diverting into the transducer chamber C. Thus, once the system is filled, further fluid flow is maintained through the flow path 22. The acoustic waves 18 generated by the ultrasonic transducer 16 are directed at the flow path 22 such that the fluid F passes through the acoustic focal zone 20 created by the acoustic waves 18, the focal zone 20 being wholly within the flow path 22. Wear particles within the fluid F scatter the acoustic wave 18 and produce a pulse echo received by the ultrasonic transducer. The amplitude of the echo is analyzed to determine the size of the wear particle. The ultrasonic transducer 16 has the ability to detect all solid debris, both metallic and non-metallic. This ability to detect all types of solid debris is important because the working components of modern machinery are often formed of or coated with or otherwise present both metallic and non-metallic wear particles into lubricating oil or other fluid.

The flow path 22 is vital to the operation of the apparatus 10 because it ensures that the fluid F flows through the acoustic focal zone 20 of the transducer 16. The acoustic focal zone 20 has a non-uniform hourglass shaped acoustic intensity profile. Acoustic intensity reaches maximum at the center of the acoustic focal zone 20, and decreases to zero outside of the acoustic focal zone 20. Therefore, large wear particles in the fluid F outside of the acoustic focal zone 20 may produce a small echo, and may be counted as a small debris or may not generate an echo at all. However, because the flow path 22 is shaped to restrict the flow of the fluid having wear particles to be wholly within the acoustic focal zone 20 of the ultrasonic transducer 16, there is no worry that a wear particle would not be counted or would not be measured accurately.

FIG. 2, taken along line 2-2 of FIG. 1 shows the cross section of an embodiment of the flow path 22 of the apparatus 10, while, for comparison, FIG. 3 shows a cross section of a flow path of a prior art ultrasonic debris sensor apparatus. The flow path 22 shown in FIG. 2 is defined by a flow path structure 23, and the inlet channel 12, outlet channel 14 and flow path structure 23 are positioned relative to the ultrasonic transducer 16 so that the flow path 22 in the flow path structure 23 restricts the flow of the fluid F to be wholly with the acoustic focal zone 20. In the prior art, the flow path 22' shown in FIG. 3 is defined by flow path structure 23' in the form of a common circular conduit, and the flow path 22' is much larger than the acoustic focal zone 20' of FIG. 3. When fluid F flows through the flow path 22', only those wear particles that fall in the acoustic focal zone 20' can be detected, which will lead to an inaccurate measurement of wear particles. When fluid F flows through the flow path 22, all particles are forced to flow through the focal zone 20, and all wear particles are more accurately detected.

FIG. 2 provides a flow path 22 for a point focused ultrasonic transducer and thus has an hourglass shape. In other embodiments, a line focused ultrasonic transducer is employed and the flow path 22 has a rectangular shape. In all instances, the flow path 22 closely matches the size of the focal zone to ensure that particles in the fluid F flow through the focal zone.

The ultrasonic transducer 16 of the apparatus 10 can be either a point focused ultrasonic transducer, also known as a spherical focused ultrasonic transducer, or a line focused ultrasonic transducer, also known as a cylindrical focused ultrasonic transducer. As the names suggest, a point focused ultrasonic transducer forms a focal point and a line focused ultrasonic transducer forms focal line. Point focused ultrasonic transducers are commonly used to inspect smaller targets and line focused ultrasonic transducers are typically used to detect targets in a flat plane. Line focused ultrasonic transducers have a larger sensing zone so they have the ability to process more samples. Point focused ultrasonic transducers, on the other hand, have a smaller sensing zone than a line focused ultrasonic transducer, but with the smaller sensing zone comes higher sensitivity, which is important to being able to detect small wear particles. By detecting smaller sized wear particles in the fluid F, the user will be able to detect problems earlier and potentially catch and stop problems before they become a major issue. The actual focal zone of a point focused ultrasonic transducer is an area which surrounds the focal point and is where the most energy is located. The focal zone 20 of the point focused ultrasonic transducer 16 is shaped like an hourglass. The acoustic energy within the hourglass region does not vary much, and because of that the flow path 22 is shaped like an hourglass. The focal zone of a line focused ultrasonic transducer is shaped like two wedges connecting at the tip and, presents a rectangular shaped focal zone cross section at the flow path 22.

With reference to FIG. 4, a second embodiment of this invention provides an apparatus 110 for the detection of wear particles in a fluid F. This apparatus is substantially like that of FIGS. 1 and 2 though an inductive pulse sensor is added upstream of the flow path 122 at which the ultrasonic transducer 116 acts to analyze wear particulate data. Thus, the apparatus 110 includes a housing 111 having a through bore B that receives an inlet channel 112 and an outlet channel 114, with a flow path 122 defined by a flow path structure 123 between the inlet channel 112 and outlet channel 114. Fluid F having wear particles therein is fed into the inlet channel 112 from a source S2 and flows from the inlet channel 112 to the outlet channel 114 through the flow path 122. The housing 111 further includes a transducer chamber C that receives an ultrasonic transducer 116. The transducer chamber C communicates with the through bore B through a wave passage P in a wall W between the through bore B and the transducer chamber C. The ultrasonic transducer 116 creates an acoustic wave 118 that defines an acoustic focal zone 120 at the flow path 122. The flow path 122 is shaped to restrict the flow of the fluid F to be wholly within the acoustic focal zone 120 of the ultrasonic transducer 116. These elements are as described above though like parts receive like numerals but increased by 100 in the disclosure of the present embodiment. Thus further details of these elements as provided above apply here as well.

Figure 5:
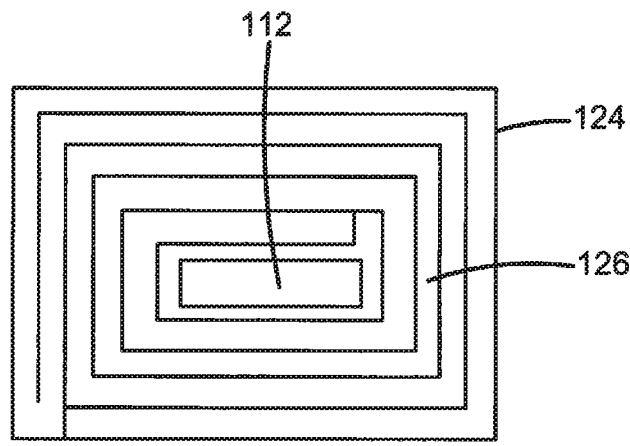
FIG. 5 is a cross section taken along the line 5-5 in FIG. 4 and showing the planar coil of the inductive pulse sensor wound about the channel defining the flow path of the fluid.

In distinction to the embodiment of apparatus 10, the apparatus 110 further includes an inductive pulse sensor 124. The inductive pulse sensor 124 includes a planar coil 126 wound around the inlet channel 112 and a detection system (not shown) for detecting metallic wear particles in the fluid as they pass through the inlet channel 112. The inductive pulse sensor 124 can only detect metallic/conductive wear particles and it can differentiate between ferrous and non-ferrous metallic/conductive wear particles. The metallic wear particles are detected based on a change in an electrical property of the planar coil 126 as metallic wear particles in the fluid F pass the planar coil 126. FIG. 5 is taken along line 5-5 of FIG. 4 and shows the cross section of the inductive pulse sensor 124. In particular, FIG. 5 shows how the planar coil 126 is wound around the inlet channel 112.

The inductive pulse sensor 124 detects and counts all metallic wear particles in the fluid, both ferrous and non-ferrous particles. An external oscillator, such as an AC source (not shown), supplies an alternating current to the planar coil 126. The AC source may be one which is able to provide a frequency of oscillation in the range of about 2 Hz-20 MHz, e.g., 100-600 KHz. The planar coil 126 may be formed from copper or other conductive metal. As shown in FIG. 5, the planar coil 126 defines a continuous strip with a plurality of concentric turns. To optimize detection of very small particles, it is desirable for the coil to have as many turns as possible in as small an area as possible. A turn is an entire 360 degree wrapping of the planar coil 126 around the inlet channel 112. While in FIG. 5, the coil is illustrated as being substantially rectangular, in other embodiments, the coil may be circular. As shown in FIG. 5, the turns of the coil 126 may have a line width of about 2 µm or greater (i.e., sufficient width to carry an electric current for producing a magnetic field) e.g., up to about 50 µm. A spacing in between turns of the coil may be about 2-100 µm, e.g., 5-10 µm.

The inductive pulse sensor 124 uses the Coulter counting principle to detect the wear particles. The Coulter principle states that as wear particles in the fluid F flow through the inlet channel 112 and passes the planar coil 126; the wear particles produce a change in an electrical property of the planar coil 126 that is proportional to the size of the wear particle passing the planar coil 126. The inductive pulse sensor 124 relies on the fact that wear particles in the fluid that pass the electric field created by the planar coil 126 will cause a measurable disturbance in the field and that the magnitude of the disturbance is proportional to the size of the wear particle.

The ultrasonic transducer 116 of the apparatus 110 has the ability to detect all solid wear particles, both metallic and non-metallic. The inductive pulse sensor 124 has the ability to detect only metallic wear particles. By comparing the results from the ultrasonic transducer and the inductive pulse sensor, the apparatus 110 is advantageously capable of differentiating and detecting the specific amount of both non-metallic and metallic wear particles in the fluid.

Figure 6:
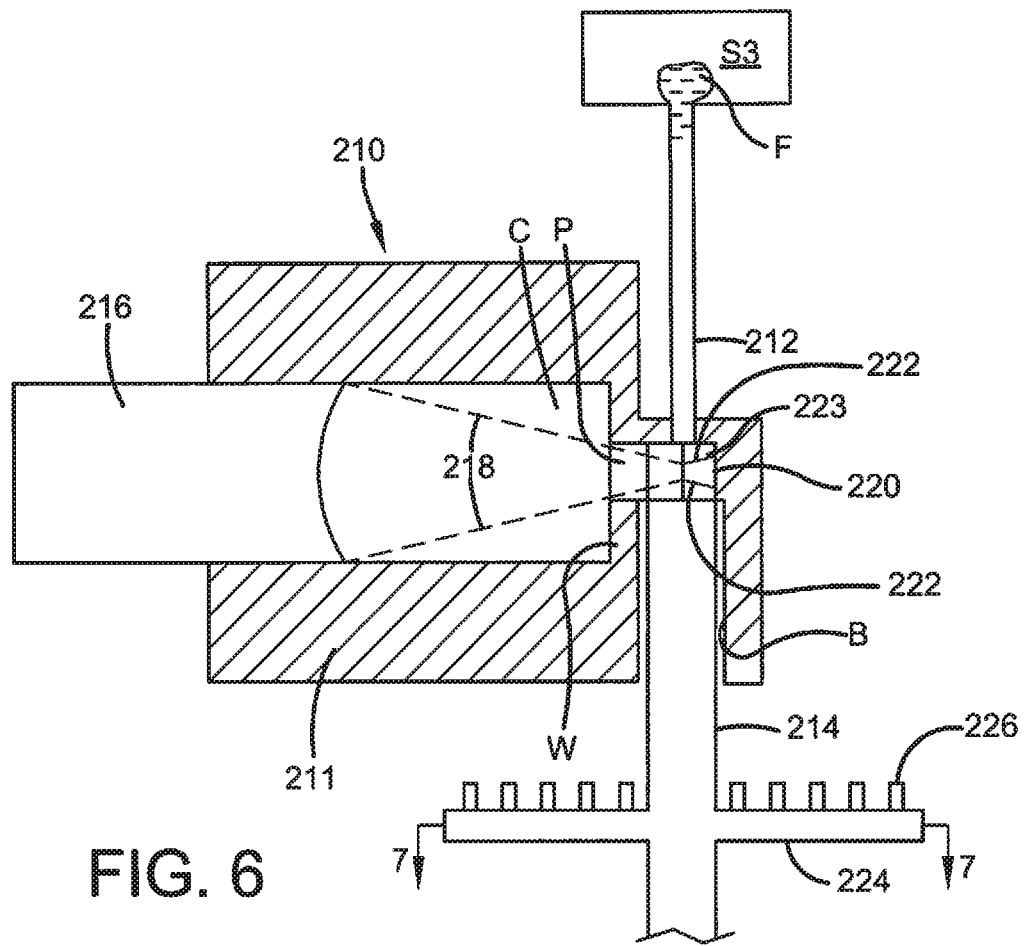
FIG. 6 is a general schematic view of an apparatus in accordance with a third embodiment of this invention, the apparatus employing an ultrasonic transducer for the detection of wear particles in a fluid and employing an inductive pulse sensor downstream of the ultrasonic transducer.

With reference to FIG. 6, a third embodiment of this invention provides an apparatus 210 for the detection of wear particles in a fluid F. This apparatus is substantially like that of FIGS. 3 and 4, though the inductive pulse sensor 224 is positioned downstream of the flow path 222 at which the ultrasonic transducer 216 acts to analyze wear particulate data. Thus, the apparatus 210 includes a housing 211 having a through bore B that receives an inlet channel 212 and an outlet channel 212, with a flow path 222 defined by a flow path structure 223 between the inlet channel 212 and the outlet channel 214. Fluid F having wear particles therein is fed into the inlet channel 212 from a source S3 and flows from the inlet channel 212 to the outlet channel 214 through the flow path 222. The housing 211 further includes a transducer chamber C that receives an ultrasonic transducer 216. The transducer chamber C communicates with the through bore B through a wave passage P in a wall W between the through bore B and the transducer chamber C. The ultrasonic transducer 216 creates an acoustic wave 218 that defines an acoustic focal zone 220 at the flow path 222. The flow path 222 is shaped to restrict the flow of the fluid F to be wholly within the acoustic focal zone 220 of the ultrasonic transducer 216.

Figure 7:
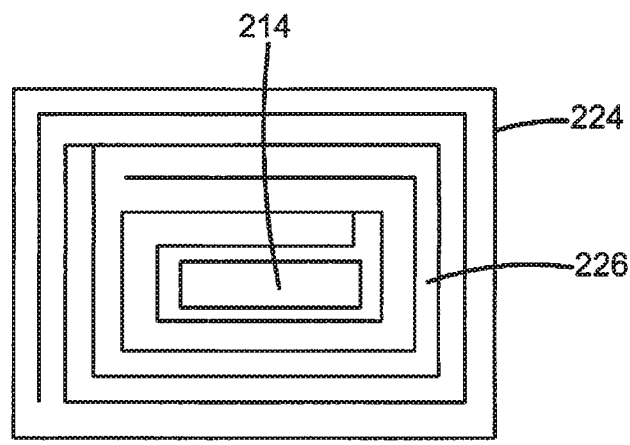
FIG. 7 is a cross section taken along the line 7-7 in FIG. 6 and showing the planar coil of the inductive pulse sensor wound about the channel defining the flow path of the fluid.

The apparatus 210 further includes an inductive pulse sensor 224. The inductive pulse sensor 224 includes a planar coil 226 wound around the outlet channel 214 and a detection system (not shown) for detecting wear particles in the fluid F as they pass through the outlet channel 214. The wear particles are detected based on a change in an electrical property of the planar coil 226 as a wear particle in the fluid passes the planar coil 226. FIG. 7 is taken along line 7-7 of FIG. 6 and shows a top down view of the inductive pulse sensor 224. In particular, FIG. 7 shows how the planar coil 226 is wound around the outlet channel 214.

Figure 8:
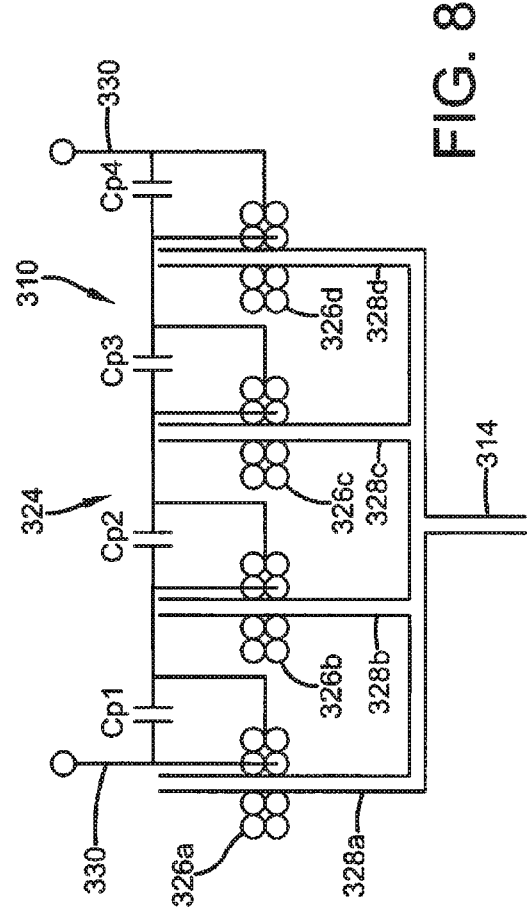
FIG. 8 is a general schematic view of an apparatus in accordance with a fourth embodiment of this invention, the apparatus employing a multichannel, multiplexed inductive pulse sensor.

With reference to FIG. 8, a fourth embodiment of this invention provides an apparatus 310 for the detection of wear particles in a fluid. The apparatus 310 includes a multichannel, multiplexed inductive pulse sensor 324 that interacts with a plurality of flow channels 328a, 328b, 328c and 328d that feed to a common outlet channel 314. A fluid F having wear particles therein is fed into the plurality of flow channels 328a-d from one or more sources (not shown) and flows from the plurality of flow channels 328a-d to the outlet channel 314. The inductive pulse sensor also includes a plurality of electrically conductive coils, such as planar coils 326a, 326b, 326c and 326d, shown in FIG. 8, each of which are respectively wound around one of the plurality of flow channels 328a-d. The plurality of planar coils 326a-d are connected to a detection system 330, and serve to detect metallic wear particles passing through the plurality of flow channels 328a-d based on a change in an electrical property of the coils 326a-d in a manner to be discussed.

Figure 9:
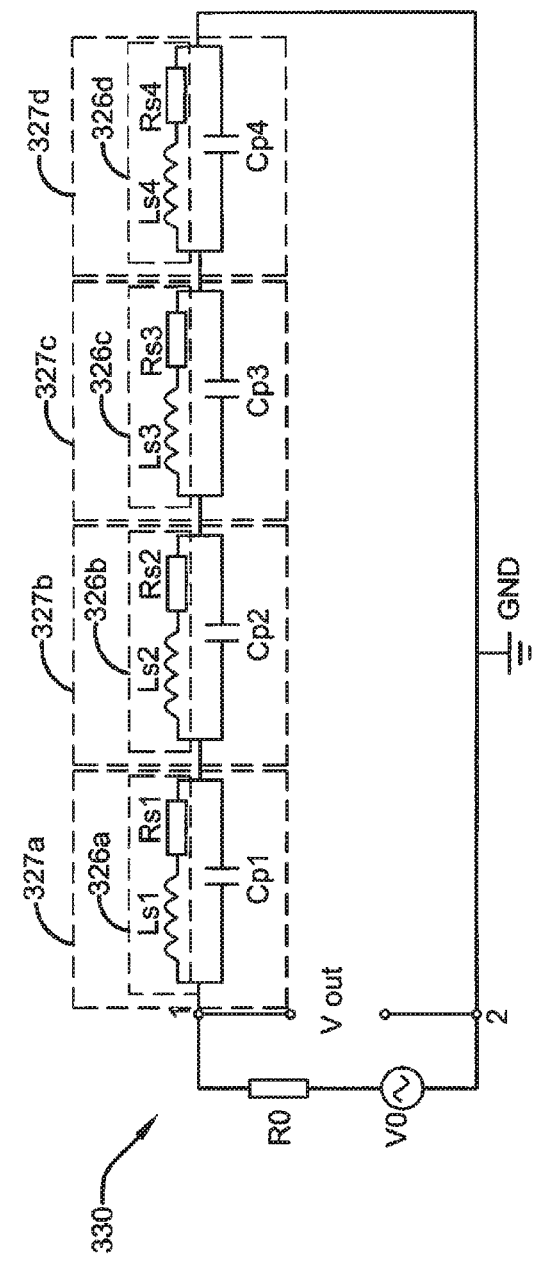
FIG. 9 provides the measurement setup and equivalent electrical circuit for the four-channel multiplexed inductive pulse sensor of FIG. 8.

Specifically, as shown clearly in FIG. 9, each of the planar coils 326a-d are connected in series with one another, whereby each planar coil 326a-d is modeled as an inductance $L_{si}$ (i=1, 2, 3, 4) in series with a resistance $R_{si}$ (i=1, 2, 3, 4). In addition, an external capacitor $C_{pi}$, (i=1, 2, 3, 4) is connected in parallel with each planar coil 326a-d, so as to form a plurality of series-coupled parallel LC resonant circuits 327a-d.

Continuing, each of the series coupled parallel LC resonant circuits 327a-d are connected to a sinusoidal excitation source $V_o$, that is in series with an internal resistor Ro, as shown in FIG. 9. Next, a specific capacitance $C_{pi}$ is selected for each LC resonant circuit 327a-d that is associated with each respective flow channel 328a-d, so that each LC resonant circuit has a unique resonance frequency. Once each the LC resonant circuits 327a-d are tuned so they have different resonance frequencies, a combined excitation signal is applied to the series coupled LC resonant circuits by the excitation source $V_o$. The combined excitation signal comprises four separate waveforms whose individual frequencies are near or close to each of the tuned resonant frequencies of the LC resonant circuits associated with each of the flow channels 328a-d. However, it should be appreciated that the excitation signal may comprise a sine wave, cosine wave, or any other suitable waveform. Upon the application of the combined excitation signal, the detection system 330 generates a combined response voltage $V_{out}$ that can be readily measured across the all of the LC resonant circuits 327a-d. In other words, the detection system 330 applies a single combined excitation signal, which includes the resonant frequency of each of the parallel LC resonant circuits 327a-d, to all of the LC resonant circuits at one time, whereupon the detection system 330 measures one single voltage output $V_{out}$ for the plurality of flow channels 328a-d. Accordingly, the voltage signals from each flow channel 328a-d exhibits a peak amplitude at its resonant frequency, so the signals for each individual flow channel 328a-d can be recovered from the combined response by taking the spectrum components at each resonance frequency with an improved signal-to-noise ratio. As a result, the change in electrical property for each planar coil 326a-d as identified by the LC resonant circuit 327a-d associated with of each respective flow channel 328a-d can be calculated from individual signals. That is, in the event of the passage of one or more wear particles through the flow channels 328a-d a change in the expected response of the LC resonant circuits 327a-d is be detected by the detection system 300.

Thus, the detection system 330 uses resonant frequency division multiplexing to simultaneously detect wear particles in a fluid passing through the channels 328-d while using only one set of detection electronics. For example, in the case of the 4-flow channel 328a-d system shown in FIGS. 8 and 9, a 300% increase in throughput is able to be achieved. Although FIGS. 8 and 9 show the use of only 4 flow channels, it is contemplated by those of skill in the art that such concept can be used for a multitude of flow channels and is not limited to just an apparatus employing only 4 flow channels. It should be appreciated that by adjusting the value of the external capacitor $C_{pi}$, the resonant frequency of each individual flow channel 328a-d can be regulated differently.

Figure 10:
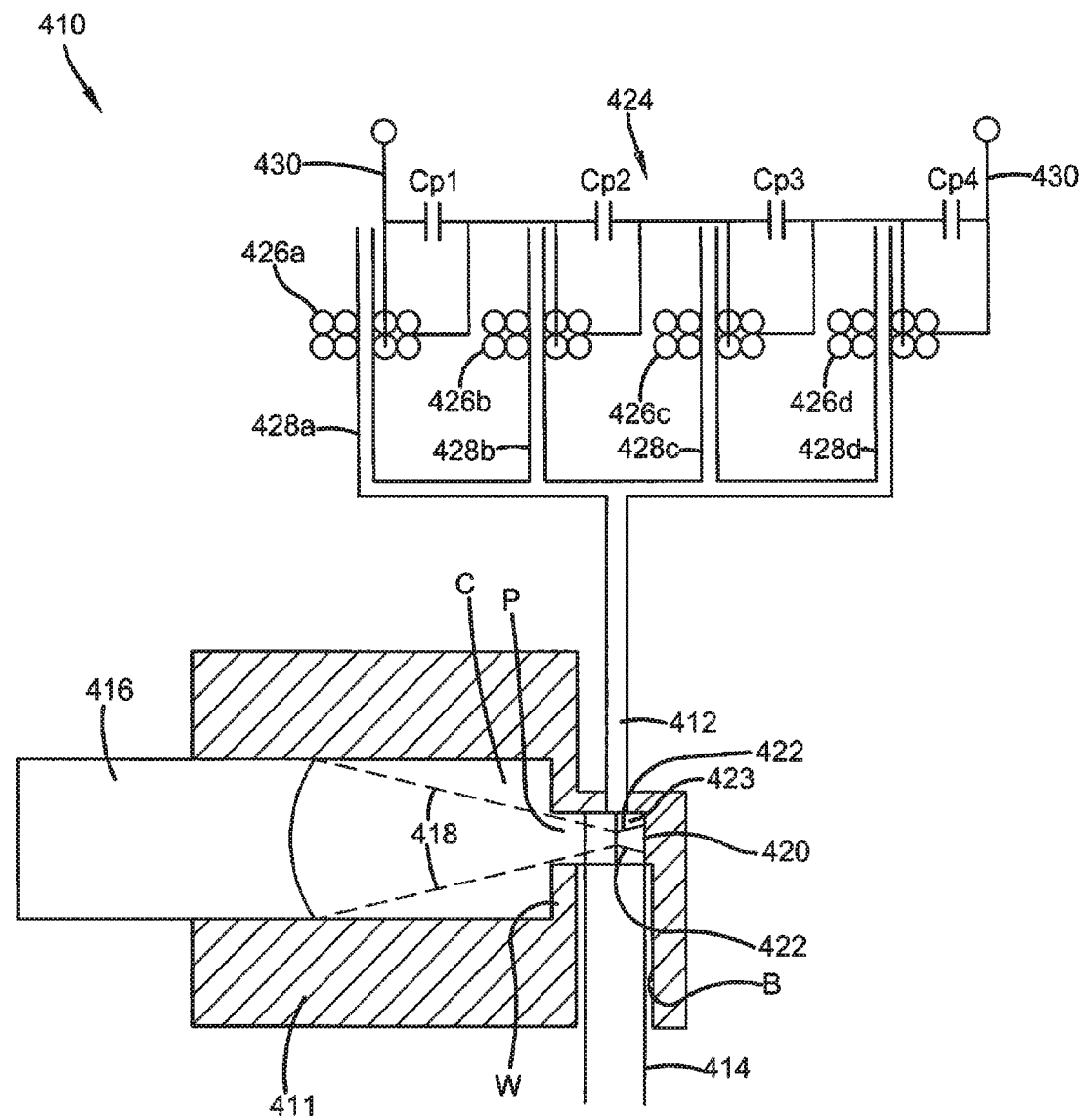
FIG. 10 is a general schematic view of an apparatus in accordance with a fifth embodiment of this invention, the apparatus employing an ultrasonic transducer for the detection of wear particles in a fluid and employing a multichannel, multiplexed inductive pulse sensor upstream of the ultrasonic transducer.

With reference to FIG. 10, a fifth embodiment of this invention provides an apparatus 410 for the detection of wear particles in a fluid. The apparatus 410 provides a combination of the above multichannel, multiplexed inductive pulse sensor apparatus (as in FIGS. 8 and 9) with the above concentrated focal zone ultrasonic apparatus (as in FIGS. 1 and 2) to provide an apparatus suitable for handling large flow rates and accurately measuring and discerning both metallic and non-metallic debris in a working fluid. Thus, the apparatus 410 includes an inductive pulse sensor 424 including a plurality of flow channels 428a, 428b, 428c, and 428d which receive a fluid F having wear particles therein. The fluid F (not shown) is fed into the plurality of flow channels 428a-d from one or more sources (not shown) and flows from the plurality of flow channels 428a-d to the inlet channel 412, which is like the outlet channel 314 of FIG. 8, but termed an inlet channel here because it serves as an inlet to the focal zone of an ultrasonic transducer, as will be described more fully below. The inductive pulse sensor also includes a plurality of planar coils 426a, 426b, 426c, and 426d wound around a respective one of the plurality of flow channels 428a-d. The plurality of planar coils 426a-d are connected in series with one another, as represented in FIG. 10, and a detection system 430 serves to detect metallic wear particles passing through the plurality of flow channels 428a-d. The detection system 430 detects wear particles based on a change in an electrical property of the plurality of planar coils 426. The detection system 430 sends a single combined excitation signal to all of the planar coils 426 at one time and the detection system 430 then measures one single output measurement for the plurality of flow channels 428. Each planar coil 426 is electrically connected in parallel with an external capacitor which is represented by $C_{pi}$ (i=1, 2, 3, 4).

The apparatus 410 also includes a housing 411 having a through bore B that receives an inlet channel 412 and an outlet channel 414 with a flow path 422 defined by a flow path structure 423 between the inlet channel 412 and the outlet channel 414. Fluid F having wear particles therein is fed into the inlet channel 412 from the plurality of flow channels 428 and flows from the inlet channel 412 to the outlet channel 414 through the flow path 22. The housing 411 further includes a transducer chamber C that receives an ultrasonic transducer 416. The transducer chamber C communicates with the through bore B through a wave passage P in a wall W between the through bore and the transducer chamber C. The ultrasonic transducer 416 creates an acoustic wave 418 that defines an acoustic focal zone 420 between the inlet channel 412 and the outlet channel 414. The apparatus 410 further includes at the flow path 422. The flow path 422 is shaped to restrict the flow of the fluid F to be wholly within the acoustic focal zone 420 of the ultrasonic transducer 416. This is the defining characteristic of the flow path 422, and it can be defined by any appropriate flow path structure 423 that confines the flow of the fluid F to be wholly within the acoustic focal zone 420. The flow path structure 423 may be a pipe of conduit and can even be an integral part of the inlet channel 412 and outlet channel 414.

Fluid F fills the transducer chamber C, inlet channel 412, flow path structure 423 and outlet channel 414, and, with the chamber C filled with fluid F, the fluid F in the transducer chamber C serves as a static barrier to urge the flow of fluid F directly from the inlet channel 412 to the outlet channel 414 through the flow path 422, without diverting into the transducer chamber C. Thus, once the system is filled, further fluid flow is maintained through the flow path 422. The acoustic waves 418 generated by the ultrasonic transducer 416 are directed at the flow path 422 such that the fluid F passes through the acoustic focal zone 420 created by the acoustic waves 418, the focal zone 420 being wholly within the flow path 422. Wear particles within the fluid F scatter the acoustic wave 418 and produce a pulse echo received by the ultrasonic transducer 416. The amplitude of the echo is analyzed to determine the size of the wear particle. The ultrasonic transducer 416 has the ability to detect all solid debris, both metallic and non-metallic. This ability to detect all types of solid debris is important because the working components of modern machinery are often formed of or coated with or otherwise present both metallic and nonmetallic wear particles into a lubricating oil or other fluid.

The flow path 422 is vital to the operation of the apparatus 410 because it ensures that the fluid F flows through the acoustic focal zone 420 of the transducer 416. The acoustic focal zone 420 has a non-uniform hourglass shaped acoustic intensity profile. Acoustic intensity reaches maximum at the center of the acoustic focal zone 420, and decreases to zero outside of the acoustic focal zone 420. Therefore, large wear particles in the fluid F outside of the acoustic focal zone 420 may produce a small echo, and may be counted as a small debris or may not generate an echo at all. However, because the flow path 422 is shaped to restrict the flow of the fluid having wear particles to be wholly within the acoustic focal zone 420 of the ultrasonic transducer 416, there is no worry that a wear particle would not be counted or would not be measured accurately. The detection system 430 of the apparatus 410 operates in exactly the same manner as the detection system 330 of the apparatus 310.

The inductive pulse sensor 424 uses the Coulter counting principle to detect the wear particles. The Coulter principle states that as wear particles in the fluid F flow through the flow channels 438a-d and pass the planar coils 426a-d; the wear particles produce a change in an electrical property of the planar coils 426a-d that is proportional to the size of the wear particle passing the planar coils 426a-d. The inductive pulse sensor 424 relies on the fact that wear particles in the fluid that pass the electric field created by the planar coils 426a-d will cause a measurable disturbance in the field and that the magnitude of the disturbance is proportional to the size of the wear particle.

The ultrasonic transducer 416 of the apparatus 410 has the ability to detect all solid wear particles, both metallic and non-metallic. The inductive pulse sensor 424 has the ability to detect only metallic wear particles. By comparing the results from the ultrasonic transducer and the inductive pulse sensor, the apparatus 410 is advantageously capable of differentiating and detecting the specific amount of both non-metallic and metallic wear particles in the fluid.

Figure 11:
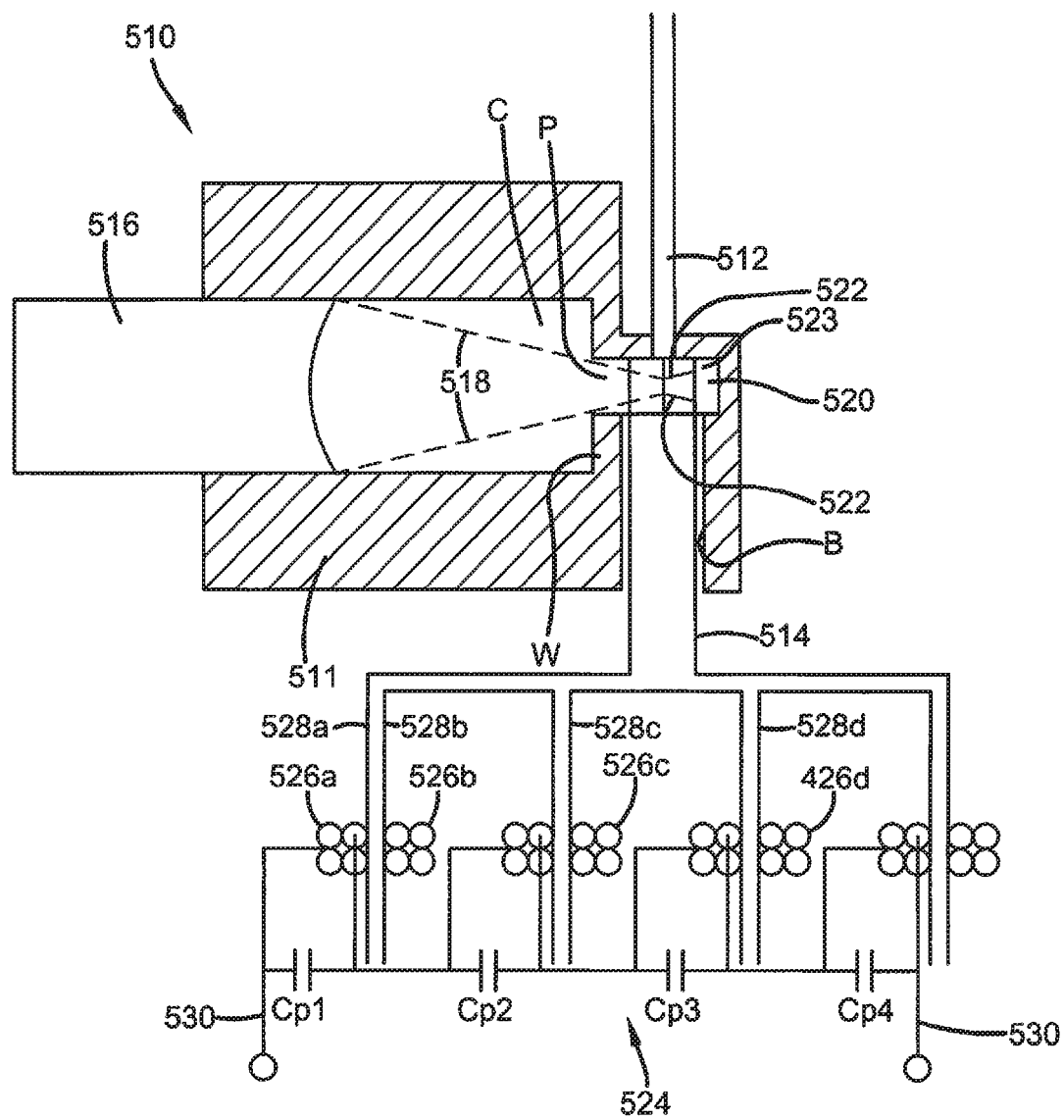
FIG. 11 is a general schematic view of an apparatus in accordance with a fifth embodiment of this invention, the apparatus employing an ultrasonic transducer for the detection of wear particles in a fluid and employing a multichannel, multiplexed inductive pulse sensor downstream of the ultrasonic transducer.

With reference to FIG. 11, a sixth embodiment of this invention provides an apparatus 510 for the detection of wear particles in a fluid F (not shown). This apparatus is substantially like that of FIGS. 10 and 11 above but for the fact that the inductive pulse sensor 524 is downstream of the flow path 522 at which the ultrasonic transducer 516 acts to analyze wear particulate data. Thus, the apparatus 510 includes a housing 511 having a through bore B that receives an inlet channel 512 and an outlet channel 514, with a flow path 522 defined by a flow path structure 523 between the inlet channel 512 and the outlet channel 514. Fluid F having wear particles therein is fed into the inlet channel 512 from a source (not shown) and flows from the inlet channel 512 to the outlet channel 514 through the flow path 522. The housing 511 further includes a transducer chamber C that receives an ultrasonic transducer 516. The transducer chamber C communicates with the through bore B through a wave passage P in a wall W between the through bore B and the transducer chamber C. The ultrasonic transducer 516 creates an acoustic wave 518 that defines an acoustic focal zone 520 at the flow path 522. The flow path 522 is shaped to restrict the flow of the fluid F to be wholly within the acoustic focal zone 520 of the ultrasonic transducer 516.

The apparatus 510 further includes an inductive pulse sensor 524. The inductive pulse sensor 524 includes a plurality of flow channels 528a-d that receives a fluid F having wear particles therein. The fluid F is fed into the plurality of flow channels 528a-d from the outlet channel 514. The inductive pulse sensor also includes a plurality of electrically conductive coils, such as planar coils 526a, 526b, 526c, and 526d, each of which are wound around the plurality of flow channels 528a-d. The plurality of planar coils 526a-d are connected to a detection system 330, and serve to detect metallic wear particles passing through the plurality of flow channels 528a-d based on a change in an electrical property of the plurality of planar coils 526a-d. The detection system 530 of the apparatus 510 operates in exactly the same manner as the detection system 530 of the apparatus 310.

In light of the foregoing, it should be appreciated that the present invention significantly advances the art by providing an integrated ultrasonic-inductive pulse sensor for the detection of wear particles that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. An apparatus for the detection of wear particles in a fluid comprising of:
   a. an inlet channel receiving a fluid having wear particles therein;
   b. an outlet channel, wherein said fluid flows from said inlet channel to said outlet channel;
   c. an ultrasonic transducer creating an acoustic wave that defines an acoustic focal zone between said inlet channel and said outlet channel; and
   d. a flow path between said inlet channel and said outlet channel wherein said flow path is defined by a flow path structure shaped to restrict the flow of said fluid to be wholly within said acoustic focal zone of said ultrasonic transducer.

2. The apparatus of claim 1 further comprising an inductive pulse sensor comprising a planar coil wound around the inlet channel and a detection system for detecting wear particles passing through the inlet channel based on a change in an electrical property of said planer coil as a wear particle passes said planar coil.

3. The apparatus of claim 1 further comprising an inductive pulse sensor comprising a planar coil wound around the outlet channel and a detection system for detecting wear particles passing through the inlet channel based on a change in an electrical property of said planer coil as a wear particle passes said planar coil.

4. The apparatus of claim 1 wherein said ultrasonic transducer is a point focused ultrasonic transducer.

5. The apparatus of claim 1 wherein said ultrasonic transducer is a line focused ultrasonic transducer.

6. The apparatus of claim 1 wherein said ultrasonic transducer is a point focused ultrasonic transducer; wherein said acoustic focal zone is in the shape of an hourglass; and
   wherein said flow path is in the shape of an hourglass.

7. An apparatus for the detection of wear particles in a fluid comprising of:
   a. an inductive pulse sensor comprising of:
      i. a plurality of flow channels receiving a fluid having wear particles therein;
      ii. a plurality of planar coils wound around said plurality of flow channels and wherein said plurality of planar coils are in series with one another;
      iii. an outlet channel, wherein said fluid flows from said plurality of flow channels to said outlet channel; and
      iv. a detection system for the detection of wear particles passing through said plurality of flow channels based on a change in an electrical property of said planar coils as a wear particle(s) passes said planar coils and wherein a single combined excitation signal is sent to all of said planar coils at once and said detection system measures one single output measurement for said plurality of flow channels.

8. An apparatus for the detection of wear particles in a fluid comprising of:
   a. an inlet channel receiving a fluid having wear particles therein;
   b. an outlet channel, wherein said fluid flows from said inlet channel to said outlet channel;
   c. an ultrasonic transducer creating an acoustic wave that defines an acoustic focal zone between said inlet channel and said outlet channel;
   d. a flow path between said inlet channel and said outlet channel wherein said flow path is shaped to restrict the flow of said fluid to be wholly within said acoustic focal zone of said ultrasonic transducer; and
   e. an inductive pulse sensor comprising of:
      i. a plurality of flow channels receiving the fluid having wear particles therein;
      ii. a plurality of planar coils wound around said plurality of flow channels and wherein said plurality of planar coils are in series with one another; and
      iii. a detection system for the detection of wear particles passing through said plurality of flow channels based on a change in an electrical property of said planar coils as a wear particle(s) passes said planar coils and wherein a single combined excitation signal is sent to all of said planar coils at once and said detection system measures one single output measurement for said plurality of flow channels.

9. The apparatus of claim 8 wherein said inductive pulse sensor is located upstream of said ultrasonic transducer.

10. The apparatus of claim 8 wherein said inductive pulse sensor is located downstream of said ultrasonic transducer.

11. The apparatus of claim 8 wherein said ultrasonic transducer is a point focused ultrasonic transducer.

12. The apparatus of claim 8 wherein said ultrasonic transducer is a line focused ultrasonic transducer.

13. The apparatus of claim 8 wherein said ultrasonic transducer is a point focused ultrasonic transducer; wherein said acoustic focal zone is in the shape of an hourglass; and wherein said flow path is in the shape of an hourglass.

14. An apparatus for the detection of wear particles in a fluid comprising of:
   a. an inlet channel receiving a fluid having wear particles therein;
   b. an outlet channel, wherein said fluid flows from said inlet channel to said outlet channel;
   c. an ultrasonic transducer creating an acoustic wave that defines an acoustic focal zone between said inlet channel and said outlet channel;
   d. a flow path between said inlet channel and said outlet channel wherein said flow path is shaped to restrict the flow of said fluid to be wholly within said acoustic focal zone of said ultrasonic transducer; and
   e. an inductive pulse sensor comprising a planar coil wound around the inlet channel and a detection system for detecting wear particles passing through the inlet channel based on a change in an electrical property of said planer coil as a wear particle passes said planar coil.

15. An apparatus for the detection of wear particles in a fluid comprising of:
   a. an inlet channel receiving a fluid having wear particles therein;
   b. an outlet channel, wherein said fluid flows from said inlet channel to said outlet channel;
   c. an ultrasonic transducer creating an acoustic wave that defines an acoustic focal zone between said inlet channel and said outlet channel;
   d. a flow path between said inlet channel and said outlet channel wherein said flow path is shaped to restrict the flow of said fluid to be wholly within said acoustic focal zone of said ultrasonic transducer; and
   e. an inductive pulse sensor comprising a planar coil wound around the outlet channel and a detection system for detecting wear particles passing through the inlet channel based on a change in an electrical property of said planer coil as a wear particle passes said planar coil.

* * * * *